United States Patent
Hughes et al.

(10) Patent No.: US 6,169,078 B1
(45) Date of Patent: Jan. 2, 2001

(54) MATERIALS AND METHODS FOR THE INTRACELLULAR DELIVERY OF SUBSTANCES

(75) Inventors: Jeffrey Allen Hughes; Fuxng Tang, both of Gainesville, FL (US)

(73) Assignee: University of Florida, Gainesville, FL (US)

(*) Notice: Under 35 U.S.C. 154(b), the term of this patent shall be extended for 0 days.

(21) Appl. No.: 09/076,468

(22) Filed: May 12, 1998

(51) Int. Cl.[7] ................................................. A61K 48/00
(52) U.S. Cl. .............................. 514/44; 514/2; 424/450; 435/455; 435/458
(58) Field of Search ........................ 514/44, 2; 424/450; 552/524; 435/458, 455

(56) References Cited

U.S. PATENT DOCUMENTS

| | | | |
|---|---|---|---|
| 5,059,421 | * 10/1991 | Loughrey et al. | 424/417 |
| 5,213,804 | * 5/1993 | Martin et al. | 424/450 |
| 5,639,473 | * 6/1997 | Grinstaff et al. | 424/450 |
| 5,656,609 | 8/1997 | Wu et al. | 514/44 |
| 5,705,151 | * 1/1998 | Dow et al. | 424/93.21 |
| 5,792,645 | * 8/1998 | Beug et al. | 435/325 |
| 5,942,634 | * 8/1999 | Siegel et al. | 552/524 |

FOREIGN PATENT DOCUMENTS

| | | |
|---|---|---|
| 9114696 | 10/1991 | (WO). |
| 9118012 | 11/1991 | (WO). |
| WO 94/13325 | * 6/1994 | (WO). |
| 9813007 | 4/1998 | (WO). |
| WO9817325 | 4/1998 | (WO). |
| 9850417 | 11/1998 | (WO). |
| 9938821 | 8/1999 | (WO). |

OTHER PUBLICATIONS

Tang et al. Biochemical and Biophysical Res. Comm., vol. 242, 141–145, 1998.*

Moradpour, D. et al., (1996) "Efficient Gene Transfer into Mammalian Cells With Cholesteryl–Spermidine" Biochemical and Biophysical Research Communications, 221:82–88.

Shen, W.C. et al., (1989) "The Intracellular Release of Methotrexate From A Synthetic Drug Carrier System Targeted to Fc Receptor–Bearing Cells" Journal of Controlled Release, 10: 89–96.

Briscoe, Page et al., (1995) "Delivery Of Superoxide Dismutase To Pulmonary Epithelium Via pH–sensitive Liposomes" American Journal of Physiology, 268 (Lung Cellular and Molecular Physiology, 12) : L374–L380.

Wang, J., Szoka, F.C.Jr., (1995) "Synthesis Of Multivalent Cationic Cholesteryl Lipids For Use As Gene Delivery Vehicles" Proceed Intern. Symp. Control.Rel. Bioact Mater., 22: 414–415.

Tang, F., Hughes, J.A. (1998) "Introduction Of A Disulfide Bond Into A Cationic Lipid Enhances Transgene Expression Of Plasmid DNA" Biochemical and Biophysical Research Communications 242: 141–145.

Shen, W.C., (1986) "Disulfide And Other Spacers For The Intracellular Release Of Drugs From Polymeric Carriers" Polymer Preprints, 27(1): 9–10.

Boutorine, A.S., E.V. Kostina (1993) "Reversible covalent attachment of cholesterol to oligodeoxy–ribonucleotides for studies of the mechanisms of their penetration into eucaryotic cells" Biochimie 75:35–41.

Caplen, N.J. et al. (1995) "In vitro liposome–mediated DNA transfection of epithelial cell lines using the cationic liposome DC–Chol/DOPE" Gene Therapy 2:603–613.

Farhood, Hassan, Remo Bottega, Richard M. Epand, Leaf Huang (1992) "Effect of cationic cholesterol derivatives on gene transfer and protein kinase C activity" Biochimica et Biophysica Acta, 1111:239–246.

Felgner et al. (1994) "Enhanced Gene Delivery and Mechanism Studies with a Novel Series of Cationic Lipid Formulations" Journal of Biological Chemistry 269(4):2550–2561.

Gao, Xiang, and Leaf Huang (1991) "A Novel Cationic Liposome Reagent For Efficient Transfection Of Mammalian Cells" Biochemical and Biophysical Research Communication 179(1):280=285.

Hermanson, G.T. (1996) In: Bioconjugate Techniques, pp. 150–152, Academic Press, San Diego.

Legendre, J.Y., A. Trzeciak, B. Bohrmann, U. Deuschle, E. Kitas, A. Supersaxo (1997) "Dioleoylmelittin as a Novel Serum–Insensitive Reagent for Efficient Transfection of Mammalian Cells" Bioconjugate Chem. 8:57–63.

Liu, Feng, Jingping Yang, Leaf Huang, Dexi Liu (1996) "New Cationic Lipid Formulations for Gene Transfer" Pharmaceutical Research 13(12):1856–1860.

Trail, P.A., D. Willner, S.J. Lasch, A.J. Henderson, S. Hofstead, A.M. Casazza, R.A. Firestone, I. Hellström, K.E. Hellström (1993) "Cure of Xenografted Human Carcinomas by BR96–Doxorubicin Immunoconjugates" Science 261:212–215.

Trail et al.(1997) "Effect of Linker Cariation on the Stability, Potency, and Efficacy of Carcinoma–reactive BR64–Doxorubicin Immunoconjugates" Cancer Research 57:100–105.

Vigneron et al. (1996) "Guanidinium–cholesterol cationic lipids: Efficient vectors for the transfection of eukaryotic cells" Proc. Natl. Acad. Sci. USA 93:9682–9686.

Zabner, Joseph, Al J. Fasbender, Tom Moninger, Kristi A. Poellinger, Michael J. Welsh (1995) "Cellular and Molecular Barriers to Gene Transfer by a Cationic Lipid" The Journal of Biological Chemistry 270(32):18997–19007.

* cited by examiner

Primary Examiner—Scott D. Priebe
Assistant Examiner—Dave Trong Nguyen
(74) Attorney, Agent, or Firm—Saliwanchik, Lloyd & Saliwanchik

(57) ABSTRACT

The subject invention concerns novel materials and methods for the delivery of substances into cells. In a specific embodiment substances are delivered into cells using a novel class of lipid compounds. These compounds, cationic lipid compounds having a disulfide bond, can be complexed with DNA to be inserted into a cell in gene therapy. Once inside the cell, enzymes present within the cell cleave the disulfide bond and the DNA is released.

3 Claims, 1 Drawing Sheet

MATERIALS AND METHODS FOR THE INTRACELLULAR DELIVERY OF SUBSTANCES

The subject invention was made with government support under a research project supported by the National Institutes of Health Grant Nos. NIH R29 HL55770-02 and NIH PO1 AG10485-06. The government has certain rights in this invention..

BACKGROUND OF THE INVENTION

Although gene therapy technology is becoming more advanced and sophisticated there are still a number of technical hurdles which limit the usefulness of this technology. One of the important technical hurdles pertains to the difficulty of delivering DNA into a cell and having that DNA reach its intended target so that genetic transformation can occur. There are several steps in this process including finding an appropriate vehicle for delivering the DNA, increasing the efficiency by which DNA enters the cell, and increasing the likelihood that the DNA will be released by the delivery vehicle so that it reaches its intended location within the cell.

The use of cationic organic molecules to deliver heterologous genes in gene therapy procedures has been reported in the literature. Not all cationic compounds will complex with DNA and facilitate gene transfer. Currently, a primary strategy is routine screening of cationic molecules looking for good candidates. The types of compounds which have been used in the past include cationic polymers such as polyethyleneamine, ethylene diamine cascade polymers, and polybrene. Proteins, such as polylysine with a net positive charge have also been used. The largest group of compounds, cationic lipids; includes DOTMA, DOTAP, DMRIE, DC-chol, and DOSPA. All of these agents have proven effective but suffer from potential problems such as toxicity and expense in the production of the agents.

Cationic liposomes are currently the most popular system for gene transfection studies. Cationic liposomes serve two functions: protect DNA from degradation and increase the amount of DNA entering the cell. While the mechanisms describing how cationic liposomes function have not been fully delineated, such liposomes have proven useful in both in vitro and in vivo studies. However, these liposomes suffer from several important limitations. Such limitations include low transfection efficiencies, expense in production of the lipids, low suspenibility when complexed to DNA, and toxicity.

Compounds containing disulfide bonds are able to participate in disulfide exchange reactions over a broad range of conditions from acid to basic pH and in a wide variety of buffer constitutes and physiological conditions (Hermanson, G. T. (1996) Bioconjugate Techniques, pp. 150–152, Academic Press, San Diego). Because of their special chemical properties, disulfide conjugate techniques have been widely used in drug delivery to achieve high delivery efficiencies (Trail, P. A., D. Willner, S. J. Lasch, A. J. Henderson, S. J. Hofstead, A. M. Casazza, R. A. Firestone, I. Hellstrom, K. E. Hellstrom (1993) Science 261:212–215; Legendre, J. Y., A. Trzeciak, B. Bohrmann, U. Deushle, E. Kitas, A. Supersaxo (1997) Bioconjugate Chem. 8:57–63; Kostina, E. V., A. S. Boutorine (1993) Biochimie 75:35–41; Trail, P. A., D. Willner, J. Knipe, A. J. Henderson, S. J. Lasch, M. E. Zoeckler, G. R. Braslawsky, J. Brown, S. J. Hofstead, R. S. Greenfield, R. A. Firestone, K. Mosure, K. F. Kadow, M. B. Yang, K. E. Hellstron, I. Hellstrom (1997) Cancer Research 57:100–105). The most common method used in bioconjugates involves cross-linking or modification reactions using disulfide exchange processes to form disulfide linkage with sulfhydryl-containing molecules. However, this method is not suitable for the syntheses of most cationic lipids due to their specific chemical structures. The use of cationic compounds containing disulfide bonds to deliver DNA in gene therapy procedures has not previously been described.

BRIEF SUMMARY OF THE INVENTION

The subject invention provides novel materials and methods for efficiently delivering polynucleotides or other molecules across cell membranes into intracellular regions. Advantageously, this transport of molecules from extracellular to intracellular locations is accomplished in a manner whereby the transported molecule is released in the intracellular regions and does not remain complexed or otherwise associated with a carrier molecule upon exposure to the intracellular environment. The introduction into a cell of molecules which are not associated with carrier molecules is highly advantageous because the transported molecule, free from association with a carrier molecule, is able to provide a desired biological activity without any inhibition which could be caused by a carrier molecule.

To accomplish efficient molecular transport followed by intracellular release, the materials and methods of the subject invention exploit differences which exist between intracellular and extracellular environments. A specific embodiment of the subject invention involves attaching or complexing a desired molecule with a second molecule (or other moiety) wherein said second molecule facilitates the efficient transfer of the desired molecule across a cell membrane. The association between the desired molecule and the second molecule remains intact in the extracellular environment and as the desired molecule crosses the cell membrane. However, upon exposure to the intracellular environment, the association between the desired molecule and the second molecule is broken thereby freeing the desired molecule in the intracellular space.

The desired molecules which can be transported into cells according to the subject invention include, for example, polynucleotides such as DNA or RNA. The transport of polynucleotides into target cells is necessary in a variety of procedures where it is desired, for example, to transform a target cell with heterologous polynucleotides. The efficiency of such transformation procedures can be improved by the materials and methods of the subject invention which make it possible to delivery uncomplexed polynucleotides to the intracellular environment. Such uncomplexed polynucleotides (or other desired molecules) are not hindered from performing an intended function within the cell by the presence of a carrier molecule.

In a specific embodiment, the subject invention provides a new class of lipid molecules for use in non-viral gene therapy. Advantageously, these novel compounds effectively complex with DNA and facilitate the transfer of DNA through a cell membrane into the intracellular space of a cell to be transformed with heterologous DNA. Furthermore, these lipid molecules facilitate the release of heterologous DNA in the cell cytoplasm thereby increasing gene transfection during gene therapy in a human or animal.

The novel compounds of the subject invention provide a disulfide linker between a polar head group and a lipophilic tail group of the lipid. Upon entering a cell, these lipids are exposed to high intracellular concentrations of glutathione or other reducing substances which reduce the disulfide bond thereby releasing the heterologous DNA in the cytoplasm. This process increases the efficiency of gene transfection. The lipid molecules of the subject invention are particularly advantageous because they can be selectively destabilized within the cytosol of the cell.

A further aspect of the subject invention pertains to convenient methods of synthesis for disulfide-containing cationic lipids. In a specific embodiment, the lipid, 1,2-dioleoyl-sn-glycero-3-succinyl-2-hydroxyethyl disulfide ornithine conjugate (DOGSDSO), can be synthesized and used to prepare liposomes in combination with L-dioleoyl phosphatidylethanolamine (DOPE). The disulfide bond of DOGSDSO is cleaved by reductive media leading to destabilization of the liposome/DNA complex, thus increasing the release of DNA compared to a non-disulfide-containing analog.

To demonstrate the importance of the disulfide bond a comparison was made of the gene transfection activities and the transfection efficiency of the disulfide bond containing-cationic lipid DOGSDSO, its analog 1',2'-dioleoyl-sn-glycero-3'-succinyl-1,6-hexanediol ornithine conjugate (DOGSHDO) which has a similar structure to DOGSDSO but does not contain a disulfide bond, and commercially available 1,2-dioleoyl-3-trimethylammonium-propane (DOTAP). In all liposome preparations the cationic lipid was mixed with an equal molar ration of DOPE. Lipid/DNA complexes were treated either with media containing 10 mM DTT or DTT free-media for 12 hours at 37° C. to evaluate the dissociation of DNA from complexes in reductive media. Only DNA complexed by DOGSDSO/DOPE liposomes and treated with DTT was released. DNA complexed by DOGSHDO/DOPE liposome was not released in either environment. Without treatment of DTT, no DNA was released from the DOGSDSO/DOPE/DNA complex after incubation for 12 hours at 37° C. This indicates that the dissociation of DNA from lipid complexes is difficult and may act as a barrier for gene transfection. When exposed to high concentrations of intracellular reductive substances, the disulfide bond of DOGSDSO is reduced and DNA released resulting in higher plasmid DNA concentrations within the cytoplasm and greater production of the transgene.

Thus, in one embodiment, the materials and methods of the subject invention exploit differences between intracellular and extracellular environments with regard to the presence of glutathione. High levels of glutathione in intracellular spaces results in the reduction in disulfide bonds which have been introduced between the desired molecule and the second molecule or moiety. The reduction of the disulfide bond inside a target cell frees the desired molecule from the carrier molecule or moiety.

Similar transport and release of desired molecules can be achieved according to the subject invention using systems which exploit other differences between intracellular and extracellular environments. Thus, in another embodiment of the subject invention, the desired molecule is attached to a second molecule such that the attachment is stable in the extracellular high sodium environment but the attachment is broken and the desired molecule is released in the low sodium and/or high potassium intracellular environment.

In a further embodiment of the subject invention the association between the desired molecule and the second molecule is stable in the low viscosity extracellular spaces but, upon exposure to the higher viscosity intracellular environment, the desired molecule is released from the second molecule.

One skilled in the art, having the benefit of the teachings provided herein could readily prepare and utilize molecules and complexes having the differential stability as described herein.

ABBREVIATIONS

DOTAP: 1,2-dioleoyl-3-trimethylammonium-propane

DOPE: L-dioleoyl phosphatidylethanolamine

Figure 1:
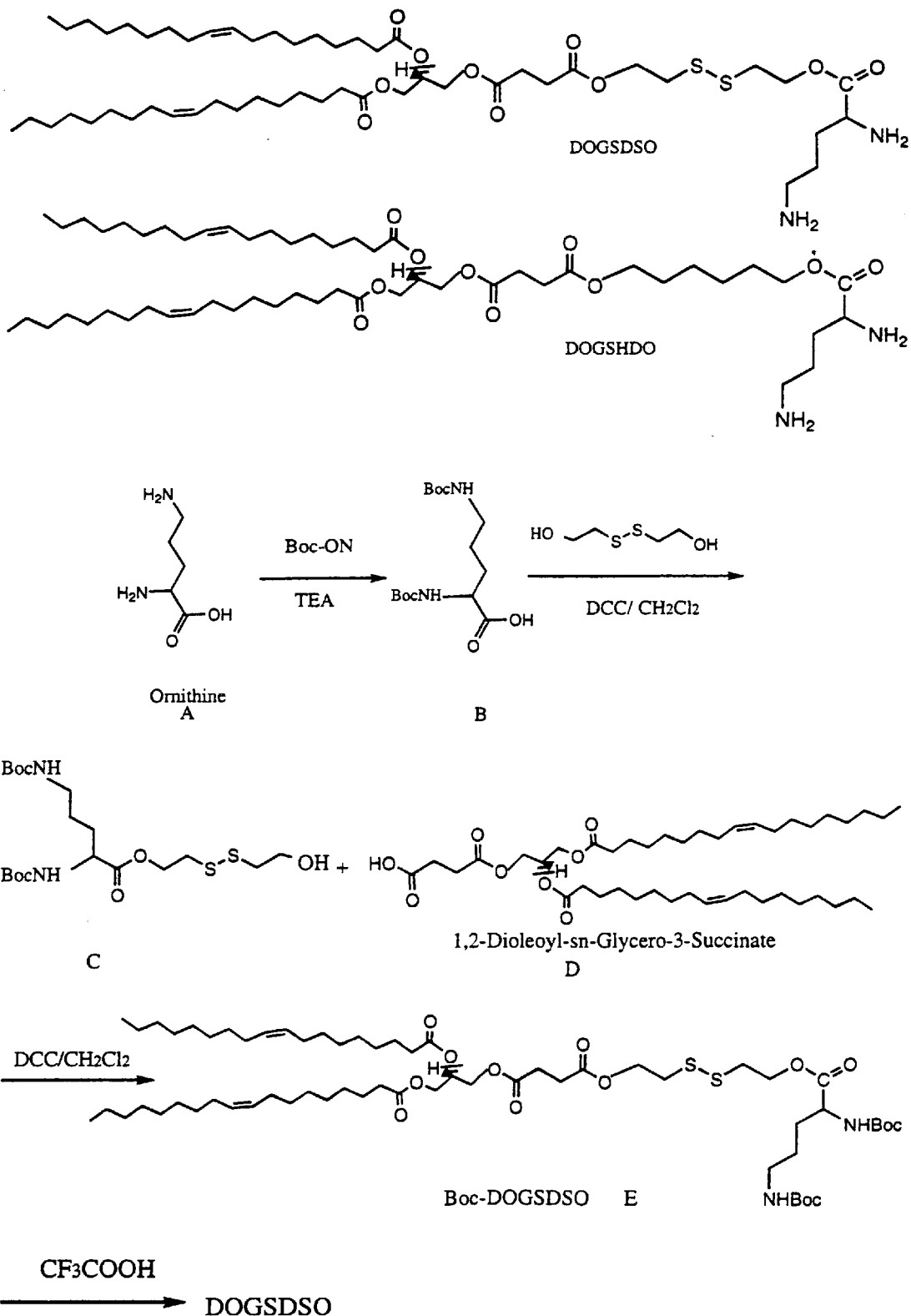
FIG. 1 shows the synthesis of DOGSDSO.

DOGSDSO: 1',2'-dioleoyl-sn-glycero-3'-succinyl-2-hydroxyethyl disulfide ornithine conjugate DOGSHDO: 1',2'-dioleyl-sn-glycero-3'-succinyl- 1,6-hexanediol ornithine conjugate

DETAILED DISCLOSURE OF THE INVENTION

The subject invention provides materials and methods useful for transporting substances into the cytosol of target cells. Advantageously, the subject invention makes it possible to efficiently deliver desired molecules across the cell membrane of a target cell and then release the desired molecule within the cell. The materials and methods of the subject invention take advantage of differences in the intracellular and extracellular environments. More specifically, the molecule which is to be delivered to the target cell (the desired molecule) is attached to a second molecule (or moiety) in a manner which achieves a stable association in the extracellular environment. Upon entering the cytosol of the cell, however, the association is disrupted thereby releasing the desired molecule within the cytosol of the target cell.

The second molecule (or other moiety), to which the desired molecule is attached (or otherwise associated) advantageously facilitates the transfer of the desired molecule across the cell membrane. The second molecule (or other moiety) is also referred to herein as the transport molecule. Together, the transport molecule and the desired molecule form a transport complex. In a specific embodiment, the transport molecule can be, for example, a cationic lipid. Specifically exemplified herein are systems whereby cationic lipids are associated with DNA molecules to facilitate the transport of the DNA into intracellular regions. This embodiment of the subject invention is highly advantageous in procedures in which transformation of a target cell with heterologous DNA is desired.

The subject disclosure provides specific examples of means for associating the desired molecule to the second molecule, for example, the use of disulfide bonds which are reduced in the intracellular environment is specifically exemplified. Those skilled in the art having the benefit of the instant disclosure will appreciate that other means for attaching the desired molecule to the second molecule or moiety can be utilized.

As used herein, reference to the "attachment" of the desired molecule to the second molecule or moiety refers to any means for associating these two chemical species such that the combination of the two species facilitates transfer of the desired molecule (and, typically, the transport molecule) across the cell membrane. This association between the two chemical species may be in the form of an ionic or covalent bond or as a complex or liposome. One specific form of attachment as contemplated by the subject invention involves the use of a cationic liposome as the transport molecule to transport DNA into a cell. In this embodiment the DNA is carried in the endosome of the liposome. Regardless of the exact nature of the attachment of the desired molecule to the second molecule or moiety, it is necessary for the attachment to be effectively broken upon entering the cell so as to release the desired molecule within the cell. Specifically exemplified herein is the use of a disulfide bond within a cationic lipid molecule in order to deliver DNA to a target cell. Upon crossing the cell membrane and entering the cytosol the disulfide bond is exposed to intracellular species which reduce the disulfide bond thus releasing the DNA into the cytosol.

Utilizing the teachings provided herein, the skilled artisan could use alternative forms of association which are stable outside the cell but are broken inside the cell. For example, the attachment may be stable in high sodium conditions (which are typical outside the cell) but are broken in low sodium/high potassium environments found inside cells. Alternatively, the attachment may be stable in low viscosity environments (typical outside the cell) and broken upon exposure to high viscosity conditions inside a cell.

As used herein, reference to the "desired molecule" means any molecule for which transport into a cell is desired. This can be, for example, polynucleotides (such as DNA) or proteins.

In a specific embodiment, the subject invention concerns novel lipid molecules for use in non-viral gene therapy. In this embodiment, the subject invention further concerns methods of preparing novel compounds and the use of these compounds in non-viral gene therapy.

The materials and methods of the subject invention can be used to improve the efficiency of DNA delivery when cationic compounds are used to transport DNA into cells. The subject invention provides a unique and advantageous delivery system which carries the DNA into the cell and then releases the DNA once inside the cell. Specifically, the DNA is complexed with a cationic lipid compound having a disulfide bond. Once inside the cell, enzymes, such as glutathione, present within the cell cleave the disulfide bond and the DNA is released.

Cationic liposomes are promising non-viral systems for use in gene delivery. Although the biochemical and biophysical mechanisms of cationic liposome assisted gene transfection and expression are not thoroughly understood, the barriers involved in the transfection process in vitro generally include the following events (1) formation of the liposome/DNA complex; (2) entry of the complex into a cell; (3) escape of DNA from the endosome; (4) dissociation of DNA from the liposome; (5) entry of DNA into the nucleus; and (6) DNA transcription. Some of the barriers can be addressed by rationale design of the delivery systems (1–5) while others (6) relate to the innate properties of the plasmid itself (e.g., promoters, enhancers etc.).

A conflict is encountered overcoming the first and fourth barriers. Cationic liposomes are required not only to complex DNA in the extracellular environment so that the DNA is protected from nucleases and enabling them to enter the cell, but also to easily release the DNA for integration and expression. To address this problem, the subject invention provides new lipids including, for example, 1',2'-dioleoyl-sn-glycero-3 '-succinyl-2-hydroxyethyl disulfide ornithine conjugate (DOGSDSO). This lipid contains a reversible disulfide bond between the polar head group of the lipid and its lipophilic tail. After forming the lipid/DNA complex and transporting DNA into cells, DOGSDSO is acted upon by a relatively high intracellular concentration of reductive substances which cleave the disulfide bond, thus releasing the DNA. This causes a higher cytoplasm concentration of DNA and an increase in transgene expression.

The subject invention also provides new methods for the synthesis of cationic lipids containing a disulfide bond. In a specific embodiment the cationic lipid is DOGSDSO.

In one series of experiments the transfection activity of DOTAP/DOPE, DOGSDSO/DOPE, and DOGSHDO/DOPE liposomes was tested in three cell lines. In initial experiments, the optimum concentration of DOGSDSO/DOPE was determined and used for these studies. When other concentrations of the lipid were used in transfection, a similar trend was always seen but with different magnitudes of transgene expression. The importance of the disulfide bond in the lipid structure was evaluated by comparing the transfection efficiency of DOGSDSO to the structural analog, DOGSHDO. DOTAP/DOPE was evaluated as a second control liposome composed of a commonly used cationic lipid. DOGSDSO/DOPE demonstrated greater transgene expression than DOTAP/DOPE in all cell lines tested. In the cell lines tested there was a significant difference between treatment with DOGSDSO/DOPE and the other two formulations while there was no significant difference between DOTAP/DOPE and DOGSHDO/DOPE treatments. Compared to its analog, DOGSHDO, which has very similar structure except for the lack of a disulfide bond, DOGSDSO has a greater than 50-fold effect on transfection activity in 293 cells and COS-1 cells and a 4 fold increase in SKnSH cells.

In additional to its high transfection activity in the absence of serum, DOGSDSO was found equally active in the presence of 10% FBS in COS-1 cells.

The correlation of dose of DNA/liposome complexes with transgene expression is also an important aspect to reflect transfection efficiency of cationic liposomes. The optimal ratio of DNA/liposome, 2 $\mu$g of DNA transferred by DOGSDSO reached the saturation of system in COS-1 cells. With further increases of dose, there was no significant increase of luciferase activity. However, 7 $\mu$g of DNA transferred by DOGSHDO did not reach the saturation and the transgene expression was only one third of that of 2 $\mu$g of DNA transferred by DOGSDSO liposome. This characteristic of DOGSDSO makes it very advantageous for gene therapy because the toxicity of cationic liposomes is one of the drawbacks of cationic liposome-mediated gene transfer and highly efficient vectors with relatively small doses are needed for clinical applications.

Using a calcein release assay cell viability of the three cell lines was tested. In two of the cell lines (293 cells and SKnSH cells) there was a significant difference between all three treatments while in the COS cells treatment with DOGSDSO/DOPE was only significantly different from treatment with DOTAP/DOPE liposomes. The toxicity results suggest DOGSDSO/DOPE liposomes did not improve transfection activity solely through its difference in toxic effects thus suggesting that DOGSDSO/DOPE liposomes improve transfection activity by the specific mechanism of releasing the DNA in the reductive environment of the cytoplasm, although other mechanisms such as increased cellular uptake or endosomal escape may be involved.

DOGSDSO and DOGSHDO were found to have very similar three dimensional structures. The steric energy for the frame of DOGSDSO and DOGSHDO is also similar (1:61.054 kcal/mole and 1:64.971 kcal/mole, respectively). Thus, the introduction of the disulfide bond does not make a substantial difference in these physical characteristics between DGOSDSO and its analog DOGSHDO.

The optimal ratio of DOTAP to DNA in transfection was 1:1 or 2:1 (w/w). Theoretically, at the weight ratios of 1:1 and 2:1, the charge ratio of the complexes are about 1:2, 1:1 (+/−), respectively, which means complexes at these weight ratios are negatively or neutrally charged. These results seem to conflict with previous studies, which suggest that cationic lipid-mediated gene transfection is efficient when the lipid/DNA complexes have a net positive charge that can associate with anionic residues on the cell membrane (Felgner, J. H., R. Kumar, C. N. Sridhar, C. J. Wheeler, Y. J. Tsai, R. Border, P. Ramsey, M. Martin, P. L. Fengler (1994) *J. Biol. Chem.* 269:2550–2561; Gao, X. and L. Huang (1991) *Biochem. Biophys. Res. Commun.* 179:280–285; Zabner, J., A. J. Fasbender, T. Moninger, K. A. Poellinger, M. J. Welsh(1995)*J. Biol. Chem.* 270:18997–19007;Vigneron, J. P., N. Oudrhiri, M. Fauquiet, L. Vergely, J. C. Bradley, M. Bassevill, P. Lehn, J. M. Lehn (1996) *Proc. Natl. Acad. Sci. USA* 93:9682–9686). However, in an agarose gel retardation study of complexes of DOTAP/DNA at weight ratios of 1:1 and 2:1, a relatively large amount of free pDNA was found. The zeta potential of complexes at these two ratios were +0.07 mV and +0.78 mV respectively. The result suggested the charge of the complexes was different from that of theoretical calculations and that the net charge of the complexes was still slightly positive. It was also observed that, at weight ratios of DOTAP to DNA bigger than 2:1, transfection complexes form large aggregates. Although fresh complexes were used for transfection, in 5–10 minutes after DOTAP was mixed with DNA, complexes were still found to form large aggregates in half an hour during transfection. The lack of physical stability of liposome/DNA complexes affects the gene transfection activity (Caplen, N.J., E. Kinrade, F. Sorgi, X Gao, D. Gruenert, C. Couttelle, L. Huang, E. W. F. W. Alton, R. Williamson (1995) *Gene Ther.* 2:603). However, according to the subject invention, at the high weight ratio of 10/1 (charge ratio 6/1 (+/−)), DOGSDSO and DOGSHDO did not aggregate during transfection. As compared to DOTAP, which has a quaternary amino head group, DOGSDSO and DOGSHDO have an ornithine head group which bears two primary amino groups. The interaction force between primary amino groups and DNA is not as strong as the interaction force of a quaternary amino group with DNA and is dependent on the local environment.

Materials and Methods

Chemicals: DOTAP, DOPE, and 1,2-dioleoyl-sn-glycero-3-succinate were purchased from Avanti Polar Lipids (Alabaster, Ala.). Calcein-AM was purchased from Molecular Probes, Inc. (Eugene, Oreg.). Other organic reagents were bought from Aldrich Chemicals (Milwaukee, Wis.).

Plasmid DNA: All supplies were purchased from Promega (Madison, Wis.). Plasmid DNA was obtained from E. coli (strain JM-109) which had been transfected with a pGL3 luciferase producing plasmid. Plasmid DNA was isolated using a Megawizard DNA purification kit. The concentration and purity of pDNA were determined spectrophotometrically.

Synthesis of DOGSDSO (FIG. 1): Amino groups of L-ornithine were protected with Boc-ON in wet 1,4-dioxane to produce B (Itoh, M., D. Hagiwara, T. Kamiya (1977) *Bulletin of the Chemical Soc. of Japan* 50(3):718–721). B was esterified with 5 equivalents of 2-hydroxyl disulfide to form C (DCC, 1.1 equiv., RT, in $CH_2Cl_2$) (Hassner, A. and V. Alexanian (1978) *Tetrahedron Letters* 46:4475–4478). C and D (1:1) were condensed to generate Boc-DOGSDSO (DCC, 1.1 equiv., RT, in $CH_2Cl_2$). Thin layer chromatography (TLC) was used to follow all the reactions. A normal separation method of silica gel chromatography was used to purify B, C, D and E. The molecular weight of E was determined by ionization spray positive mode mass spectrometry, MW=1171 (calculated 1171.7 for $C_{62}H_{110}N_2O_{14}S_2$). $^1H$ NMR ($CDCl_3$, 300 HZ): 0.90 [t, 2'($CH_3$)], 1.20–1.69[m, 26'($CH_2$)], 1.44[s, 2'($CH_3$)$_3$ ], 2.01 [q, 4'(C=C—$CH_2$) ], 2.31 [m, 2'($CH_2$C=O)], 2.71 [s, O=C$CH_2$$CH_2$C=O], 2.91 [t, $CH_2$SS$CH_2$], 3.12 [q, $CH_2$N], 4.18 [m, a-H], 4.36 [2'(CH=CH)], 4.62 [broad s, NH], 5.05–5.12[broad s, NH], 5.22–5.40 [m, O$CH_2$CHOC$H_2$O]. Before using the lipid to prepare liposomes, E was deprotected ($CF_3$COOH, 0° C., 15min) (Behr, J. P. (1989) *J. Chem. Soc., Chem. Commun.* 101–103), and excessive trifluoroacetic acid was dried under high vacuum to yield DOGSDSO. The overall yield was 45%–50% based on the amount of starting amino acid. Because DOGSDSO was unstable on silica during chromatography, its purity was checked by TLC, and it was used directly to prepare liposomes. A similar synthetic method and conditions were used to synthesize the non-sulfide analog DOGSHDO with similar chemical yields.

Liposome preparation: DOTAP, DOGSDSO, and DOGSHDO were dissolved and mixed with a neutral lipid DOPE (1:1 molar ratio) (Felgner, J. H., R. Kumar, C. N. Sridhar, C. J. Wheeler, Y. J. Tsai, R. Border, P. Ramsey, M. Martin, P. L. Fengler (1994) *J. Biol. Chem.* 269:2550–2561) in chloroform. The solution was evaporated in a round-bottom flask using a rotary evaporator at room temperature. The lipid film was dried by nitrogen for an additional ten minutes to insure all solvent was evaporated. The lipid film was then suspended in sterile water to make a concentration of 1 mg/ml based on the amount of DOTAP, DOGSDSO or DOGSHDO. The resultant mixtures were shaken for 30 minutes, followed by sonication by using Sonic Dismembrator (Fisher Scientific) for 5 minutes at 5 watts to form homogenized liposomes. The particle size distribution of the liposomes was measured using a NICOMP 380 ZLS instrument (Santa Barbara, Calif.) with the volume-weight distribution parameter. The average diameter of all liposomes was between 220–350 nm regardless of the cationic lipid used. The liposomes were stored at 4° C. until use. The liposomes demonstrated similar transfection activity when used for gene transfection for up to two months when stored under these conditions.

Dissociation of DNA from the lipid/DNA complex in reductive media: One microgram of DNA was complexed with 16 mg DOGSDSO/DOPE or DOGSHDO/DOPE in PBS (1 mL) (pH=7.4). After the initial mixing, the complexes were incubated for 30 minutes at room temperature. DL-Dithiothreitol (DTT) in PBS (pH=7.4) was then added to complexes to form a final concentration of 10 mM. The mixtures were incubated for 12 hours at 37° C. Released plasmid DNA from the complex was visualized by SYBR staining of a 0.7% TBE agarose gel.

Cell culture and transfection: SKnSH cells, HEK 293 cells, and COS-1 cells (obtained through ATCC) were maintained in RPMI 1640, DMEM, and DMEM (high glucose) respectively, and supplemented with 10% fetal bovine serum and antibiotics (penicillin 100 mg/ml and streptomycin 100 mg/ml). All cells were maintained in 5% $CO_2$ and at 37° C. in humidified air. Cell lines were cultured and seeded in 24 well plates ($2 \times 10^5$ cells/ well) and grown to 60–80% confluence in 1 ml of media with serum. pDNA/lipid complexes were made and incubated at room temperature in serum free media for 30 minutes and used for transfection. Before transfection, serum containing media was changed to serum free media and the transfection mixtures were added to the cells. After 4.5 hours, the media was changed to growth media containing serum, and the cells were grown for another 48 hours. Firefly luciferase activity was measured using a luciferase assay. Following transfection and incubation, cells were rinsed twice with phosphate buffer saline. 100 ml of luciferase lysis buffer (0.1 M potassium phosphate buffer pH 7.8, 2 mM EDTA, 1% Triton X-100, 1 mM DTT) was added to the cells. The cells were lysed by shaking at room temperature for 15 minutes. Luciferase activity was quantified by using a Monolight 2010 Luminometer. 100 ml of luciferase assay buffer (30 mM Tricine, 3 mM ATP, 15 mM MgSO$_4$, 10 mM DDT, pH=7.8) and 20 ml of cell lysate were added to a 100 ml injection of 1 mM D-luciferin, pH=6.3 (Molecular Probes, Eugene, Oreg.). The light emission over a 10 second reaction period was integrated. The total protein concentration in the cell lysate was measured by the BCA protein assay reagent (Pierce, Rockford, Ill.). Luciferase activity in cultured cells was expressed as relative light units (RLU) per mg of protein. Experiments were done in quadruplicate with each experiment repeated at least twice.

In another set of experiments COS 1 and Chinese hamster ovary (CHO) cells were maintained in DMEM (high glucose) and (-MEM) respectively, and supplemented with 10% fetal bovine serum (FBS) and antibiotics (penicillin 100 g/ml and streptomycin 100 μg/ml). All cells were kept in 5% CO$_2$ and at 37° C. in humidified air. Cell lines were cultured and seeded in 24 well plates (2×10$^5$), and grown to 60–80% confluence in 1 ml of media with serum. DNA/lipid complexes were made and incubated at room temperature in serum free media for 5–10 minutes and used for transfection. Before transfection, growth media containing serum was changed to serum free media and for the experiment to test serum sensitivity, growth media were changed to fresh growth media and the transfection mixtures were added to the cells. After a certain period of time for the specific experiments, the media was changed to growth media containing serum, and the cells were grown for another 48 hours. Following transfection and incubation, cells were rinsed twice with phosphate buffer saline. 100 μL of luciferase lysis buffer (0.1 M potassium phosphate buffer pH 7.8, 2 mM EDTA, 1% Triton X-100, 1 mM DTT) was added to the cells. The cells were lysed with shaking at room temperature for 15 minutes. Luciferase activity was quantified by using a Monolight 2010 Luminometer. 100 l of luciferase assay buffer (30 mM tricine, 3 mM ATP, 15 mM MgSO$_4$, 10 mM DDT, pH=7.8) and 2 μL of cell lysate were added to a 100 l injection of 1 mM D-luciferin, pH=6.3 (Molecular Probes). The light emission over a 10 second reaction period was integrated. A standard curve of relative light units (RLU) versus luciferase was made by using a dilution series of purified firefly luciferase and showed that the linear range of light detection extends from 1×10$^3$ to 1×10$^7$. 2 l of cells lysate was used for luciferase assay. The total protein concentration in the supernatant was measured by the BCA protein assay reagent (Pierce, Rockford, Ill. ). Luciferase activity in cultured cells was expressed as RLU per mg of protein. Each experiment was repeated at least twice, and within in a series, experiments were done in triplicate.

Transfection efficiency assay: The optimal weight ratio for transfection of each liposome was used. 3 μg per well of pUF2 DNA was complexed with 30 μg of DGSDSO/DOPE, 30 μg of DOGSHDO/DOPE, and 6 μg of DOTAP/DOPE, respectively. Complexes were incubated with CHO cells in serum free media for 4.5 hour then the media was changed to growth media and further incubated for 20 hours. Transfection efficiency was determined by counting the number of green fluorescence cells compared with all cells in the field of vision under (20 magnification using a Nikon Diaphot inverted microscope). Each transfection was done in triplicate and three separate counts were made for each well.

Toxicity assay: The cellular toxicity of DOGSDSO/DOPE, DOGSHDO/DOPE and DOTAP/DOPE in the three cell lines was determined by using a calcein release assay (Lichtenfels, R., W. E. Biddison, H. Schulz, A. B. Vogt, R. Martin (1994) *J. Immunological Methods* 172:227–239). Before the assay, cells were plated in a 96 well plate (1×10$^5$/well) and grown to 60–80% confluence. Cells were treated with media containing increasing amounts of liposome and incubated for an additional 48 hours. After specific treatments, cells were washed three times with PBS and incubated with 100 ml of calcein-AM (1 mg/ml in PBS) for 30 minutes at room temperature. Calcein fluorescence intensity was measured at the excitation and emission wavelengths of 485 nm and 538 nm respectively, on a Perkin Elmer LS 50B Spectrophotometer. Cell survival was calculated as a percentage using the following equation:

$$\text{Percentage of Cell Survival} = \frac{\text{Measured Signal} - \text{Minimum Signal}}{\text{Maximun Signal} - \text{Minimum Signal}} \times 100$$

The maximum signal was the fluorescence signal obtained from cells not treated by liposomes. The minimum signal was the background signal.

Statistical analysis: Statistical are performed using two way ANOVA (Stat View 4.53, Abacus Concepts, Inc., Berkeley, Calif.). A probability of less than 0.05 was considered to be statistically significant.

Following are examples which illustrate procedures for practicing the invention. These examples should not be construed as limiting. All percentages are by weight and all solvent mixture proportions are by volume unless otherwise noted.

Example 1—Synthesis of disulfide bond-containing lipids

The subject invention provides new methods to synthesize disulfide bond-containing cationic lipids without using general bioconjugation techniques in which disulfide bonds are introduced by a disulfide-containing agent. In a specific example, 2-hydroxyethyl disulfide, cystamine, and dithiodiglycolic acid are used to directly conjugate a hydrophobic lipid portion and a hydrophilic cationic portion to produce a disulfide bond-containing cationic lipid which can be used as described herein to transport desired molecules across a cell membrane. Three examples of synthesis procedures are as follows:

(I) lipid—COOH+HOCH$_2$CH$_2$—S—S—CH$_2$CH$_2$OH+ HOOC-cationic portion→ 2-hydroxyethyl disulfide lipid—COO—CH$_2$CH$_2$—S—S—CH$_2$CH$_2$—OOC-cationic portion;

(II) lipid—COOH+H$_2$NCH$_2$CH$_2$—S—S—CH$_2$CH$_2$NH$_2$+HOOC-cationic portion→ cystamine lipid—CONH—CH$_2$CH$_2$—S—S—CH$_2$CH$_2$—NHOC-cationic portion;

(III) lipid—OH+HOOC(CH$_2$)$_n$—S—S—(CH$_2$)$_n$COOH+ H$_2$N-amine→ dithiodiglycolic acid; lipid—OOCCH$_2$—S—S—CH$_2$CONH-amine.

wherein n=1–4

Example 2—Preparation of Compounds of FIG. 1

The compounds of FIG. 1 can be prepared as follows. Amino groups of L-ornithine can be protected with Boc-ON in wet 1.6-dioxane to produce B. B was esterified with 5 equivalent of 2-hydroxyl disulfide to form C (DCC, 1.1 equiv., RT, in Ch$_2$Cl$_2$). C and D can be condensed to generate Boc-DOGSDSO(DCC, 1.1 equiv., RT, in CH$_2$Cl$_2$). A normal separation method of silica gel chromatography can be used to purify B, C, D, E. Finally, E can be deprotected (CF$_3$COOH, 0° C., 15 min), and excessive TFA dried under high vacuum to prepare DOGSDSO. Since DOGSDSO is not stable on silica during chromatography, its purity can be checked and it can be by TLC used directly to form liposomes. The same conditions can be used to synthesize the analog DOGSHDO.

Example 3—Preparation of Liposomes

DOGSDSO/DOPE: 0.1 mmol is dissolved in 20 ml of chloroform in a 100 ml round bottom flask. The chloroform is removed by the use of a rotary evaporator at elevated temperatures (40° C.) resulting in a thin, well dispersed film in the bottom of the flask. Sterile water (10 ml) is then added to the flask and sonicated with a probe sonicator (power) until the mixture is clear.

When the liposomes are sized using a dynamic light scattering system a 200 nm particle distribution is observed.

Example 4—Comparison of gene transfection activity of DOGSDSO/DOPE with DOGSHDO/DOPE and DOTAP/DOPE The ratio of cationic lipid to DNA is an important factor for gene transfer. Comparison experiments were done by using a fixed amount of DNA (3 g/well). Transfection activity of six ratios of cationic lipid to DNA: 1/1, 2/1, 3/1, 4/1, 8/1, and 10/1 (w/w) were tested in COS 1 cells and CHO cells. The molecular weight of DOGSDSO and DOGSHDO is 971.64 Dalton and 935.57 Dalton respectively. The molar ratio or charge ratio of cationic lipid to DNA of DOGSDSO and DOGSHDO is very similar if they have same weight ratio to DNA. Since serum was reported to decrease the transfection activity of some cationic liposomes, transfection was studied both in serum free media and growth media containing 10% of FBS.

With the transfection in serum free media, both DOGSDSO and DOGSHDO reached the highest transfection activity at the weight ratio of cationic lipid to DNA of 10/1 (charge ratio, 6/1 (+/−)). Further increases in the amount of liposome caused cytotoxicity and decreased the transfection activity. DOTAP reached optimal transfection activity at the weight ratio of 1:1 or 2:1 (charge ratio, 1/2, 1/1(+/−)). At the optimal ratio of each liposome, the transfection activity of DOGSDSO was 11 times higher than its analog DOGSHDO and 6 times higher than the highest transfection activity of DOTAP (at the weight ratio 1:1) in COS 1 cells. In CHO cells, at the optimal ratio of each liposome, DOGSDSO showed 3 times higher transfection activity than DOGSHDO and 2 times higher than DOTAP.

When pDNA was transferred in the growth media, the time used for incubation of cells with transfection complexes was 12 hours. DOGSDSO demonstrated high transfection activity in COS 1 ($5.9 \times 10^8$ RLU/mg protein) and was comparable to transfection activity in serum free media. When the ratios of DOGSDSO to DNA were 1/1, 2/1, 3/1, and 4/1(w/w), the expression of luciferase protein was not statistically different ($p>0.2782$), suggesting the system reached saturation. The highest transfection activity of DOGSDSO was 3 times higher than that of DOGSHDO and 2 times higher than that of DOTAP in COS 1 cells. In CHO cells, the transfection was inhibited by serum to some degree, the optimal transfection activity of all three liposomes in serum was about three times lower than that in serum free media. However, when compared to each other, the optimal transfection activity of DOGSDSO was still 3 times higher than the optimal transfection activity of DOTAP or DOGSHDO.

Example 5—Transgene expression efficiency

The transgene expression of green fluorescence protein of DOGSDSO/DOPE, DOGSHDO/DOPE and DOTAP/DOPE were studied by using the optimal transfection ratio of each liposome in CHO cells. The efficiency of DOTAP, DOGSDSO, and DOGSHDO was 5–6%, 20–25%, and 6–7% respectively. These results were consistent with those of luciferase gene expression experiments.

Example 6—Transfection activity of liposomes as a function of time

When DNA transfection was carried out in serum free media, the DNA/liposome complexes usually incubated with cells for about 4–5 hours. This period of incubation time was selected based on two facts: a) it was reported most of the complexes are internalized by 6 hours (Zabner, J., A. J. Fasbender, T. Moninger, K. A. Poellinger, M. J. Welsh (1995) *J. Biol. Chem.* 270:18997–19007),b) with further increases in incubation time without serum, the cells lack growth nutrition and are more vulnerable to toxicity of complexes and, therefore, the cell viability decreases (Farhood, H., R. Bottega, R. M. Epand, L. Huang (1992) *Biohim. Biophys. Acta* 1111, 239–246). For gene transfection in growth media containing 10% FBS, the toxicity of complexes may be alleviated, and also the transfection may be inhibited by enzymes or slowed down by negatively charged macromolecules. Both transfection of DOGSDSO and DOGSHDO reached the highest transfection activity at 12 hour transfection time in CHO cells ($p<0.0001$). With further increases in incubation time, transfection activity decreased. The decrease of transfection activity may be caused by the cytotoxicity of DNA/liposome complexes. However, the transfection activity of DOTAP was not statistically different from 2 hours to 48 hours transfection time ($p>0.1220$). With DOTAP/DNA at the weight ratio of 4/1, transfection complexes formed large aggregates in half an hour during transfection.

Example 7—Transgene expression as a function of the amount of DNA/liposomes complex Transfection activity of different formulations of cationic liposomes are usually studied either by fixing the amount of DNA or fixing the amount of cationic liposomes and changing the ratios of liposome to DNA (Felgner, J. H., R. Kumar, C. N. Sridhar, C. J. Wheeler, Y. J. Tsai, R. Border, P. Ramsey, M. Martin, P. L. Fengler (1994) *J. Biol. Chem.* 269:2550–2561; Gao, X. and L. Huang (1991) *Biochem. Biophys. Res. Commun.* 179:280–285; Zabner, J., A. J. Fasbender, T. Moninger, K. A. Poellinger, M. J. Welsh (1995) *J. Biol. Chem.* 270:18997–19007;Vigneron, J. P., N. Oudrhiri, M. Fauquiet, L. Vergely, J. C. Bradley, M. Bassevill, P. Lehn, J. M. Lehn (1996) *Proc. Natl. Acad Sci. USA* 93:9682–9686; Liu, F., J. Yang, L. Huang, D. Liu (1996) *Pharmaceutical Research* 13:1856–1860; Farhood, H., R. Bottega, R. M. Epand, L. Huang (1992) *Biochim. Biophys. Acta* 1111, 239–246). The transgene expression results are usually a roughly bell shaped curves. It is generally agreed that the low activity of low lipid/DNA ratios is due to reduced cell membrane binding, and the decline in transfection activity at high ratios reflects toxic effects of cationic lipids. The weight ratios of DOGSDSO/DNA and DOGSHDO/DNA were fixed at the optimal ratio of 10/1, and treated $2\times10^5$ COS 1 cells and CHO cells with increasing amounts of DNA/liposome complexes. The gene transfection by DOGSDSO is very efficient in COS 1 cells, where system reached saturation at 2 g of DNA. With a further increase of DNA from 2 g to 7 g, there was no significant increase of transgene expression ($p>0.2319$). Different from that of DOGSDSO, the transgene expression mediated by DOGSHDO increased with the increase of DNA/DOGSHDO complexes ($p<0.0071$) for the system did not reach saturation. When DOGSDSO was used as a transfection vector in COS 1 cells, luciferase gene expression of 2 g of pDNA was 3 time higher than that of 7 g of pDNA by using DOGSHDO as a vector (1.18E+09/3.84E+08).

For transfection in CHO cells, DOGSDSO also showed a higher transfection efficiency that DOGSHDO. The system reached saturation when 5 µg of DNA was transferred by 50 µg of DOGSDSO. There was no significant difference of gene expression between the treatments of 5 µg of DNA and 6 µg of DNA (p>0.6528). Further increase of DNA to 7 µg resulted in a decrease of gene expression (p<0.0232). The decrease may be caused by the toxic effect of complexes. Furthermore, gene expression kept increasing with an increase in the amount of DNA/DOGSHDO liposome and the trend was the same as that in COS 1 cells. 5 µg of DNA transfected by DOGSDSO resulted 14 times higher luciferase gene expression than that of 7 µg of DNA transferred by DOGSHDO (9.03E+08/6.5E+07). Toxicity of cationic liposomes and DNA/liposome complexes Cytotoxicity of DOTAP/DOPE, DOGSDSO/DOPE, and DOGSHDO/DOPE and their DNA complexes were studied in CHO cells. Liposomes of DOTAP/DOPE had the highest toxicity at the high concentration of 75 µg/ml (p<0.0220). Toxicity of DOGSDSO/DOPE and DOGSHDO/DOPE were not statistically significantly different at high concentration of 75 µg/ml (p>0.9839). After liposomes were complexed with DNA, the toxicity of liposomes was masked and was lower than the toxicity of cationic liposome alone. At high concentrations, complexes of DNA/(DOGSDSO/DOPE)had much higher toxicity than that of DNA/(DOGSHDO/DOPE) and DNA/(DOTAP/DOPE) (p<0.0022), and even statistically equaled that of DOGSDSO/DOPE(p=0.0777). The relatively high toxicity may be caused by toxicity of high concentration of transcribed luciferase protein.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of delivering a desired molecule into a cell wherein said method comprises attaching said desired molecule to a transport molecule thereby forming a transport complex wherein said transport molecule remains associated with said desired molecule in extracellular conditions and releases said desired molecule in intracellular conditions; said method further comprising contacting said transport complex with said cell, wherein said transport molecule is DOGSDSO.

2. The method, according to claim 1, wherein said desired molecule is selected from the group consisting of polypeptides and polynucleotides.

3. The method, according to claim 2, wherein said desired molecule is DNA.

* * * * *